Figure 1:
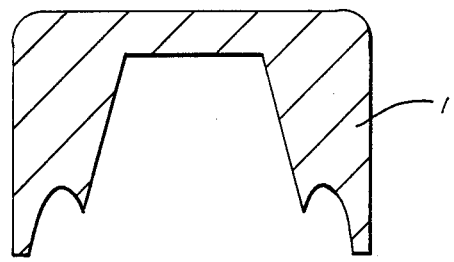
Figure 2:
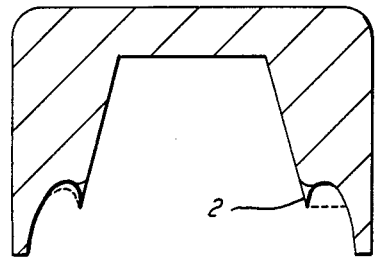
Figure 3:
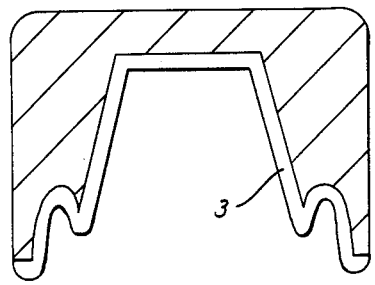
Figure 4:
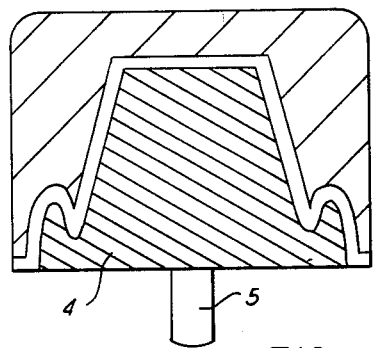

United States Patent [19]

Hornig

[11] Patent Number: 4,776,795
[45] Date of Patent: Oct. 11, 1988

[54] PROCESS FOR MAKING METAL ARTIFICIAL TOOTH PARTS

[76] Inventor: Wolfgang Hornig, Gutenbergstr. 9, 6902 Sandhausen, Fed. Rep. of Germany

[21] Appl. No.: 21,175

[22] Filed: Mar. 3, 1987

[30] Foreign Application Priority Data

Mar. 10, 1986 [DE] Fed. Rep. of Germany ....... 3607915

[51] Int. Cl.$^4$ ................................................. A61C 5/10
[52] U.S. Cl. ................................. 433/223; 433/200.1; 433/206
[58] Field of Search .............. 433/223, 74, 167, 200.1, 433/206, 208, 213, 214, 215, 218; 264/16, 17, 18, 19

[56] References Cited

U.S. PATENT DOCUMENTS

| 397,320 | 2/1889 | Ward | 433/200.1 |
|---|---|---|---|
| 1,612,605 | 12/1926 | Buenaventura | 433/200.1 |
| 3,552,018 | 1/1971 | Zahn | 433/74 |
| 3,636,632 | 1/1972 | Costa et al. | 433/213 |
| 4,363,627 | 12/1982 | Windeler | 433/223 |
| 4,562,882 | 1/1986 | Alleluia | 164/529 |

FOREIGN PATENT DOCUMENTS

| 1919652 | 11/1970 | Fed. Rep. of Germany | 433/200.1 |
|---|---|---|---|
| 3320902 | 3/1985 | Fed. Rep. of Germany | 433/206 |
| 400089 | 10/1933 | United Kingdom | 433/200.1 |

OTHER PUBLICATIONS

"Metal Sprayed Models from Elastic Impression Materials, A Preliminary Study" from British Dental Journal, Apr. 1965, S.329–332.

*Primary Examiner*—John J. Wilson
*Attorney, Agent, or Firm*—Hayes, Davis & Soloway

[57] ABSTRACT

The process for making metal artificial tooth parts consists in that an impression of the tooth or jaw to be treated is prepared using an electrically non-conductive material, the inner wall of said impression is coated with a heated low-melting alloy and then the interior is filled up with filling material in which fixing pins are inserted in the case of crowns, inlays and bridges. Alternatively, the impression is filled up with traditional filling materials and an electric conductive coating is produced by vaporizing a metal layer, spraying a conductive lacquer or currentless deposition of an electrically conductive layer. Again, alternatively the impression may be filled up with electrically conductive plastic. The positive pattern so produced is separated from the impression, and there is galvanically applied an intermediate layer of a base metal after which one or more layers of high-melting point metals are galvanically applied to the intermediate layer, the filling material, the innermost electrically conductive layer and the intermediate layer first being then removed and, if desired, porcelain and/or plastic is applied as facing or substitute teeth on the artificial tooth part thus resulting.

18 Claims, 4 Drawing Sheets

PROCESS FOR MAKING METAL ARTIFICIAL TOOTH PARTS

The invention concerns a process for making metal artificial tooth parts such as crowns, inlays, bridges, prostheses, etc., wherein an impression of the tooth or jaw to be treated is made by means of an electrically conductive material.

Those metal structures common in dental surgery are conventionally made in the casting process. Such a casting process includes a sequence of partial working cycles and thus possibilities of error, the sum total of which impairs the precision of the artificial tooth part. Besides, cast metals, insofar as the microscopic structure is concerned, shrink without homogeneity when cooling and in addition must be finished by grinding or polishing after being removed from the mold, which causes losses of material in the amount of from 10 to 15% of the cast part.

Of the high cost of production in the manufacture of artificial tooth parts, when using high-quality alloys, 60% goes to wages and 40% to the cost of materials. The wage costs increase to about 80 to 90% when alloys of less quality are used.

In order to avoid the disadvantages of cast artificial tooth parts, there has already been proposed in DE-OS No. 25 18 355 a process for the production of artificial dental structures wherein an adequate metal is electrolytically deposited on a pre-formed pattern in order to build up the artificial tooth structure on the mold thus formed. Specially for making dental crowns, there is taken an impression of the patient's tooth and a tooth pattern is made according to said impression, said pattern is metallized and introduced in an electrolyte that contains ions of the metal to be deposited so that there is electrolytically deposited on the pattern a metal layer in order to produce a mold to which porcelain is applied, after which the metal mold is finally removed from the porcelain.

Even though the process used above prevents the known difficulties that appear in casting such as the formation of cavities and the high consumption of material, it still has the disadvantage of not making possible any homogeneous, uniform galvanic deposit, since the metalizing of the patterns consisting of an electrically conductive material poses considerable problems in relation to a uniform distribution.

To avoid said difficulties, there has been disclosed in DE-OS No. 32 18 300 a process for making artificial tooth parts of metal, specially of gold, wherein a pattern of the substitute part is made, a mold is made from the pattern, in the mold a metallic casting of the pattern is produced with a machine specially developed for that, and then this metal cast is galvanically coated in a galvanization center with a mechanically cohesive layer of a noble metal in order, if desired, to provide the substitute part thus obtained, after removal from the mold, with a coating of porcelain, plastic, or the like.

The problem to be solved by this invention is to provide a simple and economical process for the manufacture of metal artificial tooth parts, wherein, without elevated cost, in particular without special galvanization centers or without casting equipment for the metal mold and therefore at a reasonable cost, it is possible to produce high-carat precision artificial tooth parts without it being necessary, as it is in the already known processes, to produce from the first pattern a second pattern in a complicated process and to build up the artificial tooth part on said second pattern.

Taking, as the point of departure, a process of the type mentioned in detail at the beginning, it is proposed for solving this problem that the inner wall of the impression be coated with a heated low-melting point alloy, and the interior is filled with filling material in which fixing pins are inserted in the case of crowns, inlays and bridges. Alternatively, the impression is filled with traditional filling matrials and an electric conductive coating is produced by vaporizing a metal layer, spraying a conductive lacquer or currentless deposition of an electrically conductive layer. Again, alternatively the impression may be filled up with electrically conductive plastic. The positive pattern so produced is separated from the impression, and there is galvanically applied an intermediate layer of a base metal after which one or more layers of high-melting point metals are galvanically applied to the intermediate layer, the filling material, the innermost electrically conductive layer and the intermediate layer first being then removed and, if desired, porcelain and/or plastic is applied as facing or substitute teeth on the artificial tooth part thus resulting.

The galvanization of different metals in the sandwich process makes possible in a heat treatment such as in the firing operation of porcelain in an alloying of the different metals and thus a control of the physical and chemical properties.

With the process according to the invention, it is possible to prepare at reasonable cost artificial tooth parts that have a great homogeneity of the metal. A saving in weight of from 70 to 80% in comparison with the casting process is easily obtainable by eliminating the finishing and losses in casting, considerable expenses can be saved. By extensive automation it is possible in the galvanization process economically to produce metal parts. Since there are eliminated in the galvanization the sources of error that appear in the casting process due to the expansion behavior of the metals when heated and to the contraction when cooled, it is possible to produce artificial tooth parts of great precision.

The substitute part in particular is produced in this process according to the first pattern, which prevents the possibility of double errors.

Figure 14:
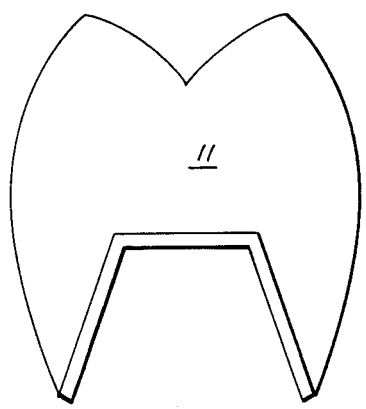
Figure 15:
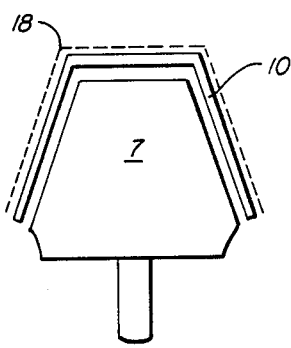
Figure 16:
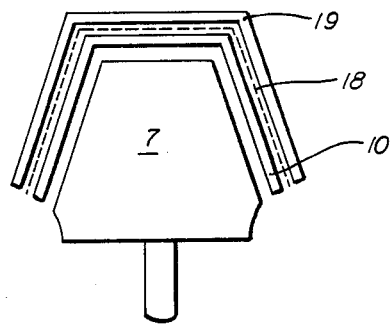
Figure 17:
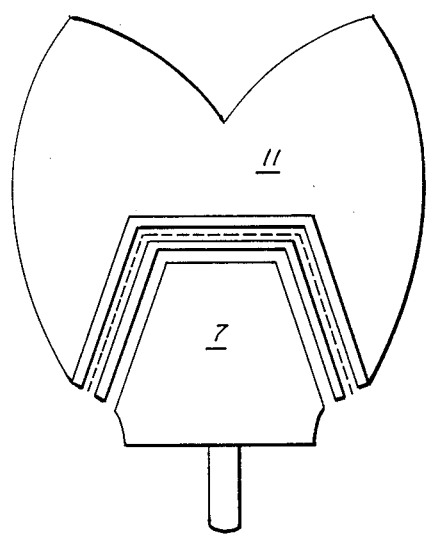

The invention will now be described, by way of example, with reference to the accompanying drawings, in which:

FIGS. 1 to 14 illustrate diagrammatically the sequence of separate process steps for making a dental crown;

FIGS. 15 to 17 diagrammatically illustrate process steps in addition to those illustrated in FIGS. 1 to 14 for making a cone crown; and FIGS. 18 to 24 diagrammatically illustrate the process steps for making a partial prosthesis.

As will be appreciated the present invention is not limited to the making of crowns and is suitable also for the production of other artificial tooth parts such as bridges, inlays, metal bases for prosthesis and cone crowns.

Figure 5:
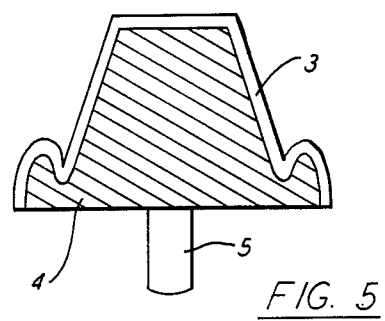

According to FIG. 1, the process of the invention for the preparation of crowns consists in that there is made with electrically non-conductive material an impression 1 of a tooth, thereafter said impression is sprayed in the area of the thin-walled spots 2 that go under the gums (FIG. 2) with an electrically conductive lacquer and then is galvanically stabilized, for instance, with copper, or is filled in the back with suitable material. According to FIG. 3, the inner wall of the impression 1 is sprayed with a heated low-melting point alloy such as lead/bismuth with a layer thickness of 0.1 to 2 mm. After said layer 3 of electrically conductive material has cooled and set, its interior is filled up with a filling material such as gypsum (FIG. 4) or plastic 4 in which one or two locking pins (dowel pin) 5 are situated. The positive pattern resulting in this manner is then separated from the impression 1. (FIG. 5)

Figure 8:
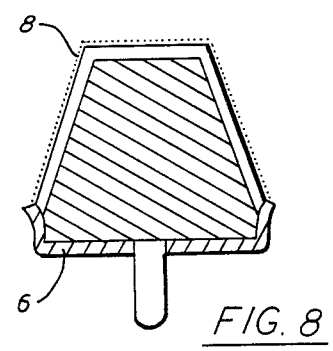

It is also possible to make an electrically conductive positive pattern from a positive pattern of traditional filling material, by coating this material to form layer 3 by vaporizing a metal, spraying a conductive lacquer or by currentless metal coating deposition thereon and then applying the intermediate layer 8 shown in FIG. 8. The impression can also be filled up with an electrically conductive plastic to produce a combination of layer 3 and filling 4. Another possibility consists in interiorly coating the impression by a currentless reduction process to produce layer 3 and then filling it up with filling material 4.

Figure 6:
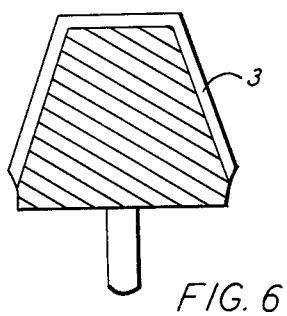

There now results an eventually necessary improvement of the surface of the positive pattern thus produced, for instance, by smoothing by means of a soldering iron. (FIG. 6).

The spots of the positive pattern 4 not to be galvanized are now provided by coating with an electrically non-conductive material (FIG. 7) after which the positive pattern thus prepared is immersed in a suitable galvanic bath in order thus to produce on the positive pattern an intermediate layer 8 consisting of a metal to be easily removed later such as copper or nickel, it being possible that the thickness of the layer 8 correspond to the intermediate space between crown and tooth stump later needed as cement gap (FIG. 8).

Figure 10:
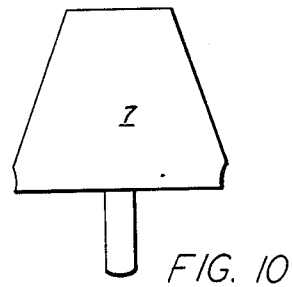
Figure 7:
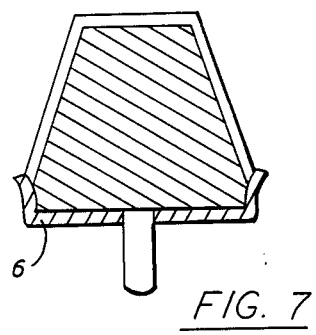
Figure 9:
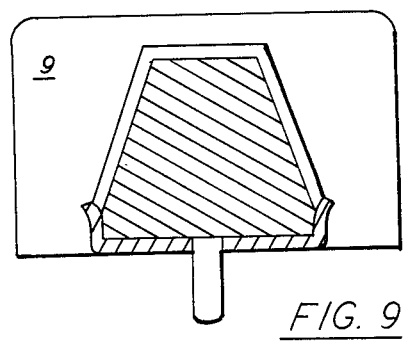

After formation of the intermediate layer 8, the pattern 4, 3, 8 is duplicated by an adequate impression material 9 to produce a second pattern 7 (FIGS. 9 and 10).

Figure 11:
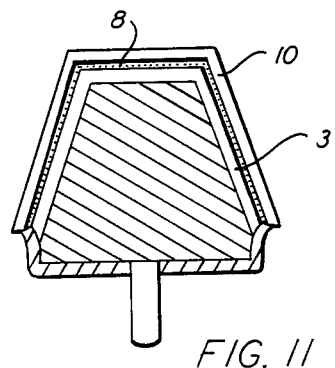

After applying the intermediate layer 8, the positive pattern with the intermediate layer is immersed in a second galvanic bath in which is present a desired alloy, or is then introduced in several different galvanic baths in order now to deposit galvanically on the intermediate layer 8 one or several layers 10 of high-melting metals, preferably noble metals such as gold. (FIG. 11).

Figure 12:
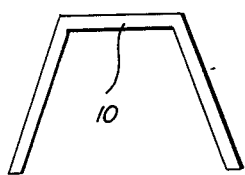
Figure 13:
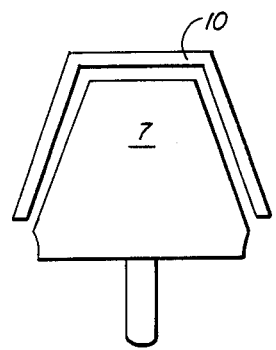

In FIG. 12, the filling material 4, the layer 3 of low-melting alloy and the intermediate layer 8 has been removed by heat or by an etching operation so that there remains a crown sleeve 10 that is superposed on the second pattern 7 produced according to FIG. 9 for further processing. (FIG. 13). For aesthetic reasons porcelain and/or plastic 11 can now be applied on this crown in a traditional manner, and for obtaining a good adhesiveness the surface of the crown sleeve 10 is roughened, for instance, by radiation with alumina, or can be prepared by silicanization. For porcelain 11 can then be fixed on the plastic applied. (FIG. 14).

According to the process of the invention bridges can also be made. Here the impression delivered by the dentist is likewise sprayed in the area of the thin-walled spots that go under the gums with an electrically conductive lacquer, and then galvanically stabilized, for instance, with copper. This impression is then sprayed on the inner walls with a layer of low-melting alloy in a thickness of about 0.1 to 2 mm, and after setting, the interior of this metal layer is filled up with gypsum or plastic. After separation from the impression, the outer wall of the alloy layer is refined, the preparation limits are defined, and the positive pattern thus resulting is duplicated with an adequate impression material, a second pattern being produced.

The required intermediate member for a bridge can be made by overgrown of finished wax parts, spraying with an electrically conductive lacquer, grinding and welding of metal finished parts or porcelain finished parts that can deflagrate, after which the spots of the electrically conductive positive pattern not to be galvanized are provided by coating with an electrically insulating material, and then coated in a suitable galvanizing bath. After galvanization the wax is melted and the hollow intermediate member is filled with facing material or, in the case of porcelain finished parts, is fired together with the firing of the facing.

When preparing a faced inlay, the inner wall of the impression is likewise sprayed with a layer of low-melting alloy in a thickness of about 0.1 to 2 mm. After filling up the hollow space with gypsum or plastic and separation from the impression, the outer wall of the positive pattern is refined, the spots of the positive pattern not to be galvanized are provided by coating with an electrically insulating substance, and then coated with metal in an adequate galvanizing bath. Porcelain or plastic is then applied in a traditional manner.

Figure 18:
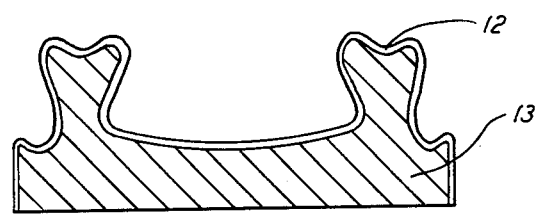
Figure 19:
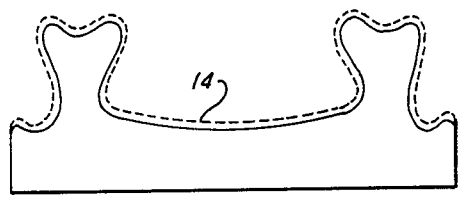
Figure 20:
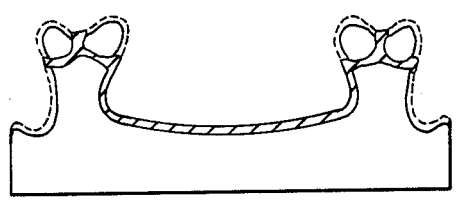
Figure 21:
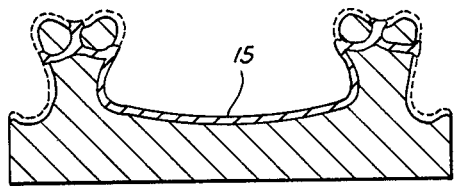
Figure 22:
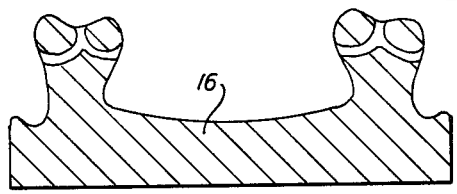
Figure 23:
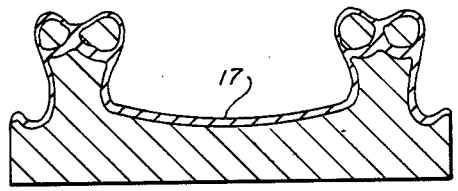
Figure 24:

According to FIGS. 18 to 24, in the process of the invention for making partial prosthesis basis, the impression delivered by the dentist is sprayed with a heated low-melting alloy 12 so that there results a metal layer about 0.1 to 2 mm thick, which after setting is filled up with a plastic or gypsum 13. (FIG. 18). The positive pattern thus obtained is separated from the impression material and refined, that is, smoothed or corrected, after which there is applied an intermediate layer 14. (FIG. 19). Thereafter it is duplicated with an adequate impression material and a duplicate is produced. Finished wax parts 15 (FIG. 20) are now deposited and the spots not to be galvanized are sprayed with an electrically insulating substance (FIG. 21) and then the wax parts 15 are removed (FIG. 22) (stencil process). The separate galvanic layers 17 are then deposited with the desired alloy, for which several galvanic baths are likewise considered. (FIG. 23). The pattern 17 is removed from the metal plate obtained by heating and the partial prosthesis base is superposed on the duplicate for further processing. (FIG. 24).

In the process according to the invention for making cone crowns, the delivered impression is likewise sprayed inside with a layer of low-melting alloy of a thickness of about 0.1 to 2 mm and separated from the impression. The low-melting metal or wax applied is now milled. Thereafter the spots not to be galvanized are produced with electrically insulated substance and the part is immersed in a suitable galvanizing bath, there being also applied here an intermediate layer with a metal to be subsequently easily removed and having a thickness which can correspond to the cement gap needed later. After applying the galvanic layers of high-melting metals such as noble metals with a thickness of 0.15 to 0.5 mm, there is additionally applied a metal layer 18 (FIG. 15) that precisely defines the subsequent discharge force between primary and secondary crown and that is easy to remove. Thereafter, the pattern thus obtained is entirely duplicated, the resulting impression is likewise sprayed with low-melting alloy in a thickness of about 0.1 to 2 mm and separated from the impression material. After the wax finished parts have been deposited and the spots not to be galvanized have been covered with an electrically insulating lacquer, the desired layers 19 (FIG. 16) are galvanically deposited with the necessary thickness and eventually facing material 11 is mounted (FIG. 17). In this construction of a partial prosthesis base, the secondary crowns are inserted as one piece. When the secondary crowns and the partial prosthesis base are separately galvanized, there takes place a subsequent welding operation in which all the other common supporting and holding elements can also be used.

Therefore, by mounting the artificial tooth parts on the first pattern, it is possible with the process of the invention to produce in a specially simple and economic manner artificial tooth parts of high precision, specially by using small galvanization instruments such as can be used in every dental laboratory or practice laboratory, and without using complicated instruments for the preparation of duplicates. The duplicates produced by the process of the invention exclusively serve as working patterns for further processing toward the final completion of the artificial tooth part but not, as in the processes known, for mounting said artificial tooth parts.

As used herein, metal shall be construed to include metal alloys.

I claim:

1. A process for preparing metal denture parts comprising the following steps:
    (a) making an impression (1), of the portion of the oral cavity to be treated using an electrically non-conductive material;
    (b) molding a positive pattern in said impression, said pattern having an electrically conductive exterior surface (3);
    (c) separating said pattern from said impression;
    (d) applying an intermediate layer (8) of a base metal to said positive pattern (3,4);
    (e) applying at least one layer (10) of the desired thickness of a high-melting point metal or metal alloy to said intermediate layer (8) to form said denture part; and
    (f) removing said positive pattern and said intermediate layer (8) from said denture part.

2. A process according to claim 1 comprising coating said impression (1) with an electrically conductive material (3) on its inner wall and filling the coated impression with a filling material (4), said coating (3) and said filling material together forming said positive pattern.

3. A process according to claim 2 wherein said electrically conductive layer (3) is a low-melting point alloy.

4. A process according to claim 3, wherein said low-melting alloy coating (3) is formed in said impression (1) with a thickness of 0.1 to 2 mm.

5. A process according to claim 1 comprising filling said impression with an electrically conductive filling material to form said positive pattern.

6. A process according to claim 1 comprising filling said impression with an electrically non-conductive filling material, removing said filling material from said impression and coating the exterior of the removed filling material with an electrically conductive material.

7. A process according to claim 1 comprising applying porcelain as a facing to the denture part.

8. A processing according to claim 1 comprising applying plastic as a facing to the denture part.

9. A process according to claim 1 wherein prior to forming said positive pattern a thin-walled area (2) of said impression (1) that goes under the gums is stabilized by backfilling.

10. A process according to claim 1, wherein prior to formation of said intermediate layer (8) on said positive pattern there is provided, on any areas not to be coated, an electrically insulating layer (6).

11. A process according to claim 1 wherein a rod is partially embedded in said filling material.

12. A process according to claim 1, wherein after removing said positive pattern and said intermediate layer (8) from said denture part (10) of high-melting point metal or metal alloy, the latter is superposed on a duplicate of said positive pattern for further processing.

13. A process according to claim 1 for preparing bridges wherein after removing positive patterns of denture parts from said impression, a bridge element to join denture parts is produced by building on a wax bridge part comprising spraying said wax part with a conductive lacquer, applying an intermediate layer on positive patterns and said bridge element, galvanizing with a high-melting point metal or metal alloy to form a combined bridge and tooth parts, removing said positive patterns, melting the wax and filling the cavity thereby left with a material mounting said denture parts together.

14. A process according to claim 1 for preparing cone crowns wherein after separating said positive pattern from said impression, a stump structure of low-melting point material needed for cone crowns is set up and is thereafter coated with electrically conductive lacquer, said intermediate layer is electrolytically built up, the stumps thus resulting are insulated on the surfaces not to be galvanized with electrically non-conductive material, a layer of high-melting point metal or metal alloy is then deposited.

15. A process according to claim 1 for preparing partial prosthesis basis, wherein after separating said positive pattern from said impression, the electrically conductive pattern is duplicated, on said primary pattern there are applied wax finished parts in the shape of the desired metal prosthesis, the spots not to be galvanized are insulated, the wax is then removed and at least one layer of high melting point metal or metal alloy is galvanically applied after which said pattern is separated from the base and superposed on said duplicate for further processing.

16. A process according to claim 1, wherein to increase the adhesiveness of a facing material, said layer (10) is roughened.

17. A process according to claim 16 wherein the roughening is achieved by spraying the surface with alumina.

18. A process for preparing metal denture parts wherein an impression of the portion of the oral cavity to be treated is prepared by means of an electrically non-conductive material, the inner wall of said impression is provided with an electrically conductive layer, and then the interior of said impression and of said layer are filled up with a filling material and at least one pin is inserted into said filling material, after which the positive pattern formed by said layer and said filling material is separated from said impression, characterized in that
    (a) an intermediate layer (8) of a base metal is galvanically applied to said positive pattern (3, 4),
    (b) one or more layers (10) of noble metals are galvanically applied to said intermediate layer (8),
    (c) said filling material (4), the innermost electrically conductive layer (3) and said intermediate layer (8) are thereafter removed, and
    (d) a facing material is applied, if desired, to the denture part that thus results.

* * * * *